United States Patent [19]

Lepie et al.

[11] Patent Number: 5,351,553
[45] Date of Patent: Oct. 4, 1994

[54] HIGH RATE FLYWHEEL TENSILE TESTING APPARATUS FOR VISCOELASTIC MATERIALS

[76] Inventors: Albert H. Lepie, 121 S. Desert Candles St.; R. Allen Boyack, 804 Ward Ave.; Frank E. Hudson, 1114 Randall St.; Larry D. Sawyer, 1248 E. Javis Ave., all of Ridgecrest, Calif. 93555

[21] Appl. No.: 59,769

[22] Filed: May 3, 1993

[51] Int. Cl.[5] ............................................. G01N 3/08
[52] U.S. Cl. ....................................... 73/826; 73/806
[58] Field of Search ................. 73/826, 828, 830, 836, 73/12.01, 834, 844

[56] References Cited

U.S. PATENT DOCUMENTS 4,266,424  5/1981  Muenstedt ............................. 73/789

FOREIGN PATENT DOCUMENTS 1190224  4/1965  Fed. Rep. of Germany ........ 73/834

OTHER PUBLICATIONS

High Strain Rate Mechanical Testing of Solid Propellants by the Hopkinson Split Bar Technique by: E. James & D. Breithaupt Feb. 16, 1984.
Jannaf Structures and Mechanical Behavior Working Group 14th Meeting 1977 vol. 1 15–17 Feb. 1977 The John Hopkins University Applied Physics Laboratory. Navy Case No. 69643 Flywheel Tensile Tester Albert Lepie.

*Primary Examiner*—Thomas P. Noland
*Assistant Examiner*—James M. Olsen
*Attorney, Agent, or Firm*—Robert J. Hampsch; Melvin J. Sliwka; John L. Forrest, Jr.

[57] ABSTRACT

A flywheel tensile testing apparatus for viscoelastic materials is used for high-rate tensile testing to determine the mechanical properties such as the initial modulus, the stress-strain characteristics, energy at break, and void formation of energetic materials such as solid propellants and plastic bonded explosives under deformation rates in excess of 20,000 inches per minute. The tensile tester is comprised of a plurality of support trestles which are mounted on a common base. A flywheel and a light weight engagement wheel are mounted for rotation on the support trestles. A clutch and rotor assembly is located between the flywheel and the light weight engagement wheel so that when the clutch is engaged, the stored energy of the flywheel is transferred to a rotor assembly which in turn drives the light weight engagement wheel. The flywheel is driven by a variable speed motor. The activation of the clutch and rotor assembly are preferably performed in response to an electronic signal. A stretching mechanism for elongating the viscoelastic test specimen is located proximate the light weight engagement wheel and further positioned so as to tangentially align the viscoelastic test specimen with the light weight engagement wheel. The light weight engagement wheel is initially in a stationary or stopped position. When activated, the light weight engagement wheel quickly ramps up to the desired speed and engages the stretching mechanism which initiates the high rate tensile test on the viscoelastic test specimen.

17 Claims, 5 Drawing Sheets

HIGH RATE FLYWHEEL TENSILE TESTING APPARATUS FOR VISCOELASTIC MATERIALS

BACKGROUND OF THE INVENTION

The present invention relates to a testing apparatus for determining the mechanical properties of viscoelastic materials and more particularly to a testing apparatus for determining the stress-strain characteristics of energetic materials such as solid propellants and plastic bonded explosives under high deformation rates up to approximately 40,000 inches per minute.

The mechanical properties of solid propellants are typically measured with an Instron tensile tester at extension rates up to 50 inches per minute or with hydraulic tensile tester for rates up to 10,000 inches per minute. In order to predict the mechanical properties of such energetic materials at higher extension rates the time-temperature superposition principle for linear viscoelastic materials is applied. To correctly apply the time-temperature superposition principle, the tensile properties of the energetic material are measured at lower strain rates at various temperatures. The Williams-Landel-Ferry (WLF) shift procedure, which is commonly known to those persons skilled in this art, is then applied to obtain a reduced master curve of the estimated tensile properties at higher extension rates at the referenced temperature. Highly filled polymers, such as solid propellants, however, often display non-linear viscoelastic behavior. Thus, the shape of the stress-strain curve at very high deformation rates or the tensile strain and energy at the break point cannot be accurately predicted using WLF shifts.

The uniaxial high extension rate properties of solid propellants and plastic bonded explosives have become important for characterizing the damage and energy absorption behavior of these materials during operational use. Damage behavior is often characterized by the presence of voids in the propellants. Since solid propellants are highly filled polymers, any finite deformation will inevitably cause high stress fields proximate the filler particles which leads to interfacial debonding, often called dewetting. Dewetting causes the formation of voids and a corresponding increase in propellant volume which can be measured with a dilatometer. At high strain rates, there is a pronounced increase in voids produced in the propellant relative to slow strain rates. Similarly, the void collapse after specimen failure is typically very fast but is also dependent on strain rate. These void formation and collapse variations are primarily due to the viscoelastic material behavior. Further study of this viscoelastic material behavior can be accomplished with the aid of a high extension rate tensile testing apparatus.

In addition, a change in the fracture mode of the propellants at high deformation rates has recently been observed and documented with the use of high speed photography. The phenomena of multiple fracture of solid propellants seems to occur at high deformation rates at ambient temperature. Above a critical stain rate, the uniaxial test specimen breaks into several pieces instead of the traditional two pieces. Empirical measurements of this viscoelastic fracture phenomena is accomplished with the use of a fully instrumented high extension rate tensile testing apparatus. Only with a high extension rate tensile testing apparatus such as the present invention can one empirically and accurately identify these critical strain rates.

Increased deformation rate testing of plasticized explosives has previously been accomplished using the Hopkinson split bar technique. See E. James and D. Breithaupy, "High Strain Rate Mechanical Testing of Solid Propellants by the Hopkinson Split Bar Technique", Lawrence Livermoore National Laboratory, UCID-20021, February, 1984. Strain rates up to 10,000 per second were obtained for impact rates up to 150,000 inches per minute. However, the small sample size typically used in Hopkinson Bar Test may give rise to significant errors.

In addition, the use of a Charpy-lzod impact pendulum for such increased deformation rate tensile testing of propellants has been attempted. See Chemical Propulsion Information Agency (CPIA) Publication 283, April 1977, pp 41-50. The straining rates attained by the Charpy-lzod impact pendulum are dependent on the length of the pendulum arm as well as the maximum release angle. Such a device is known to be suitable for extension rates up to about 12,000 inches per minute.

The use of a flywheel for impact testing of polymers is a technique that has also been previously attempted. A flywheel has certain advantages over the Hopkinson's split bar and the pendulum. The total energy losses imparted to the test specimen can easily be determined by measuring the area under the stress-strain curve or force versus extension curve. On the other hand, when employing the Hopkinson's split bar technique, the entire moving mass must be stopped after the test is completed. A significant problem with previous flywheel tensile test devices is the inability to achieve accurate tick for the engagement and disengagement of the test specimen.

The previously known flywheel type tensile testers would work in typically one of two manners. In the first arrangement, the flywheel would attain an approximate constant velocity and then the test specimen would be moved or rotated into position for engagement. The test specimen would not be engaged by the flywheel until the rotational velocity of the flywheel achieves a predetermined constant value. This test speed for a flywheel is a function of the flywheel diameter and the number of rotations per unit of time. Thus the movement or rotation of the test specimen needed to occur very quickly and synchronized with the flywheel such that the test specimen is properly engaged. For this reason, the test speed of such flywheel tensile testers has proved to be a constraining parameter because the specimen often could not properly be aligned with the engaging mechanism in sufficient time. Similar problems would be encountered if one kept the test specimen stationary and tried to move or rotate the flywheel into position for engagement.

The second alternative would be to keep the test specimen stationary but align the test specimen with the flywheel in a position suitable for engagement by the engaging claw. Since, the engaging claw is placed at a certain rotational position of the flywheel, the time available for ramping the flywheel up to a constant velocity is less than the time it normally takes for one rotation of the flywheel. Many of the flywheels used in such testing often involve a flywheel configuration having a significant mass which hindered the ability of the flywheel to attain a constant velocity prior to engaging the test specimen. Again, this situation limited the test speed of such flywheel tensile testers which in turn limits the extension rates the test specimen could be subjected to.

SUMMARY OF THE INVENTION

The present invention is a high rate tensile testing apparatus for viscoelastic materials. High rate tensile tests typically involve elongation or deformation rates in excess of 10,000 inches per minute. The preferred embodiment of the present invention as described below has performed tensile tests at elongation rates above 40,000 inches per minute and is believed to be capable of deformation rates in excess of 80,000 inches per minute.

The high rate tensile testing apparatus for viscoelastic materials as described and shown herein is comprised of a plurality of support trestles which are mounted on a common base. The flywheel is mounted for rotation on these support trestles. In addition, a light weight engagement wheel which has an engagement claw located on the outer periphery is also mounted for rotation on the support trestles. The flywheel is preferably driven by a variable speed motor which is mounted on the base. A clutch and rotor assembly is located between the flywheel and the light weight engagement wheel so that when the clutch is engaged, the stored energy of the flywheel is transferred to a rotor assembly which in turn drives the light weight engagement wheel. The activation of the clutch and rotor assembly are preferably performed in response to an electronic signal.

A stretching mechanism for elongating the viscoelastic test specimen is located proximate the light weight engagement wheel and further positioned so as to tangentially align the viscoelastic test specimen with the light weight engagement wheel and engagement claw. The light weight engagement wheel is initially in a stationary or stopped position. When activated, the light weight engagement wheel quickly ramps up to the desired speed and the engagement claw engages the stretching mechanism which initiates the high rate tensile test on the viscoelastic test specimen.

The stretching mechanism is preferably comprised of an aluminum channel guide which is mounted to the common base and dimensioned to accommodate the viscoelastic test specimen. In the channel guide is the test specimen and a length of wire having one end attached to the test specimen and the other end crimped to a roll pin which is located near the light weight engagement wheel and positioned for engagement by the engagement claw, the roll pin and length of wire are further positioned so as to tangentially align the viscoelastic test specimen with the light weight engagement wheel.

Accordingly, it is an object of this invention to provide a new and improved high rate tensile testing apparatus for testing viscoelastic materials. The tensile testing apparatus utilizes the moment of inertia from a flywheel as the driving force for measuring tensile or shear properties of viscoelastic materials at high deformation rates.

It is another object of the present invention to provide a high rate tensile testing apparatus for solid propellants and other viscoelastic materials to further aid in the study of formation and collapse of voids in such propellants when subjected to certain critical strain rates.

It is yet another object of the present invention to provide a high rate tensile testing apparatus for solid propellants and other viscoelastic materials to further aid in the study of the multiple fracture phenomena in such materials when subjected to high deformation rates.

A feature of the present invention is the novel configuration of the engagement mechanism. The flywheel first accelerates to a desired speed and then engages with a light-weight engagement wheel via a fast acting clutch. The light weight engagement wheel then reaches a constant testing speed within one revolution prior to encountering the test specimen, which is then pulled to failure.

An advantage of the present invention is that the new and improved high rate tensile testing apparatus can operate so as to test viscoelastic specimens at extension rates previously not conveniently measured. The present invention can reliably perform tensile tests on test specimens at extension rates in excess of 20,000 inches per minute.

Another advantage of the present invention is that the new and improved high rate tensile testing apparatus is relatively compact so as to easily and safely operate in a small laboratory. In addition, the fully instrumented high rate tensile testing apparatus is easy to use and capable of providing accurate and timely data on certain mechanical properties of viscoelastic material samples.

These and other objects, features and advantages of the invention are clearly evident from a thorough consideration of the figures and detailed description that follows.

DETAILED DESCRIPTION

The preferred embodiment of present invention is a flywheel tensile test apparatus for the testing of truncated and end-tabbed dogbone test specimens of viscoelastic materials to produce samples with various extent of damage. The preferred flywheel test apparatus is used for high-rate tensile testing to determine the mechanical properties such as the initial modulus, the stress-strain characteristics, energy at break, and void formation of energetic materials such as solid propellants and plastic bonded explosives under deformation rates in excess of 20,000 inches per minute.

Figure 1:
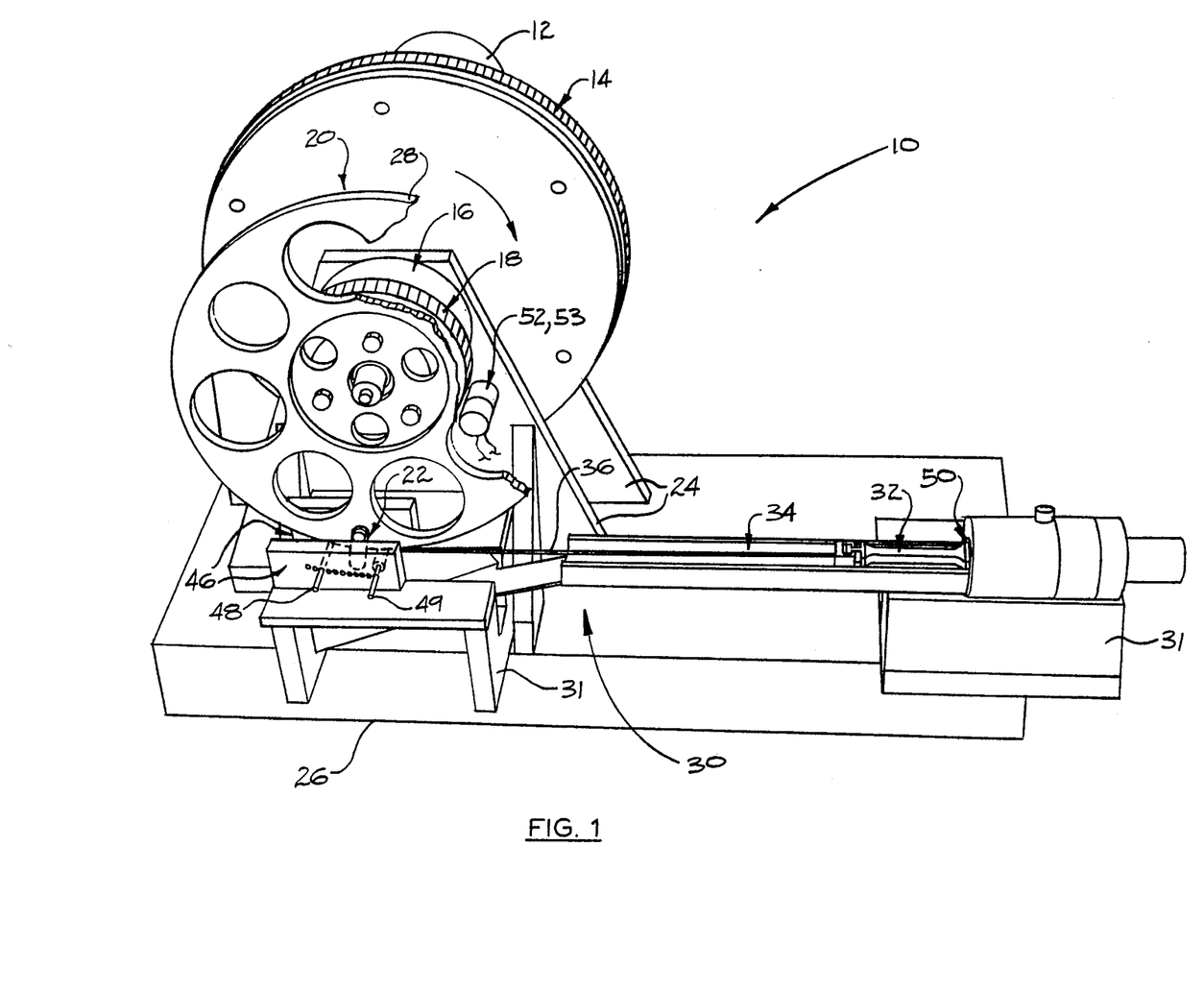
FIG. 1 is a perspective view of the preferred embodiment of the high rate tensile testing apparatus for viscoelastic materials.
Figure 2:
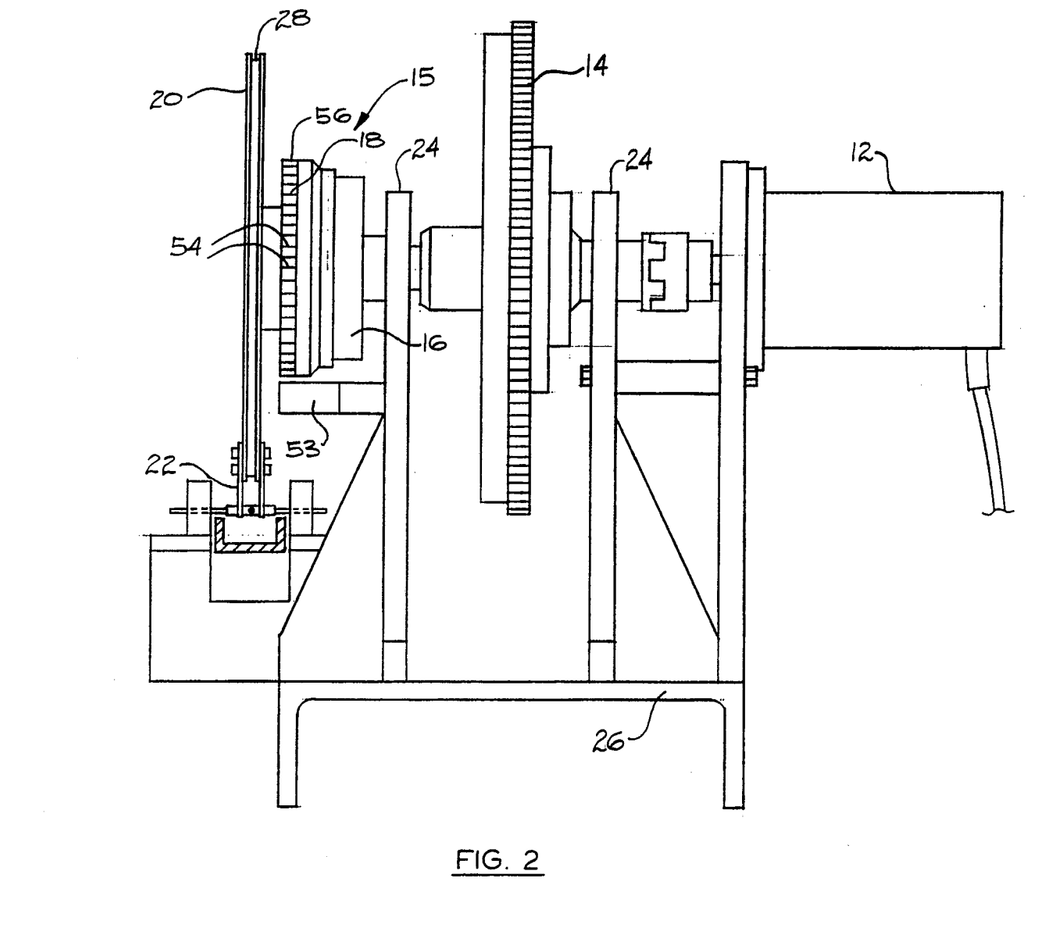
FIG. 2 is a cross section view of the present invention illustrating the flywheel, motor, support trestles, clutch and rotor assembly and the engagement wheel.

Referring to FIG. 1 and FIG. 2, the preferred embodiment of the flywheel tensile testing apparatus (10) comprises a variable speed motor (12), a flywheel (14), an electromagnetic fast acting clutch (16), a rotor assembly (18) for engaging with the electromagnetic fast acting clutch and a light weight aluminum engagement wheel (20). The testing apparatus (10) is mounted for rotation by attachment to a plurality of support trestles (24) which are mounted to a common base (26). Specifically, the flywheel (14) and the light weight engagement wheel (20) are mounted for rotation on these support trestles (24). The light weight aluminum engagement wheel (20) further has an outer diameter groove (28) and an engagement claw (22).

The flywheel (14) is preferably driven by a variable speed motor (12) which is mounted on the base (26). The clutch and rotor assembly (15) is located between the flywheel (14) and the light weight engagement wheel (20) so that when the clutch (16) is engaged, the stored energy of the flywheel (14) is transferred to a rotor assembly (18) which in turn drives the light weight engagement wheel (20). The activation of the clutch and rotor assembly (15) is in response to a predetermined and externally generated electronic signal. The preferred embodiment of the present invention utilizes a three-fourths horsepower variable speed electric motor (12) having a maximum revolutions per minute (rpm) of 1750. The flywheel (14) is a 14 inch diameter and weighs 28 pounds. The light weight engagement wheel (20) is a 12 inch diameter aluminum wheel and the engagement claw (22) extends two inches radially outward from the periphery of the engagement wheel (20). At 1750 rpm the 12 inch diameter or 6 inch radius engagement wheel and 2 inch claw can theoretically attain a maximum extension rate of 87,964 inches per minute. The maximum extension rate can be increased simply by using a larger engagement wheel, a larger engagement claw or a motor which can provide a higher rotational velocity. However, it is important to remember that the engagement wheel (20) and claw (22) must be able to achieve full rotational speed in less than one full revolution of the engagement wheel (20). It is therefore important to consider all the variables that affect the dynamics of the test apparatus including the weight of the engagement wheel (20), the diameter of the engagement wheel (20), the size of the engagement claw (22) and the rotational velocity provided by the motor (12).

Figure 3:
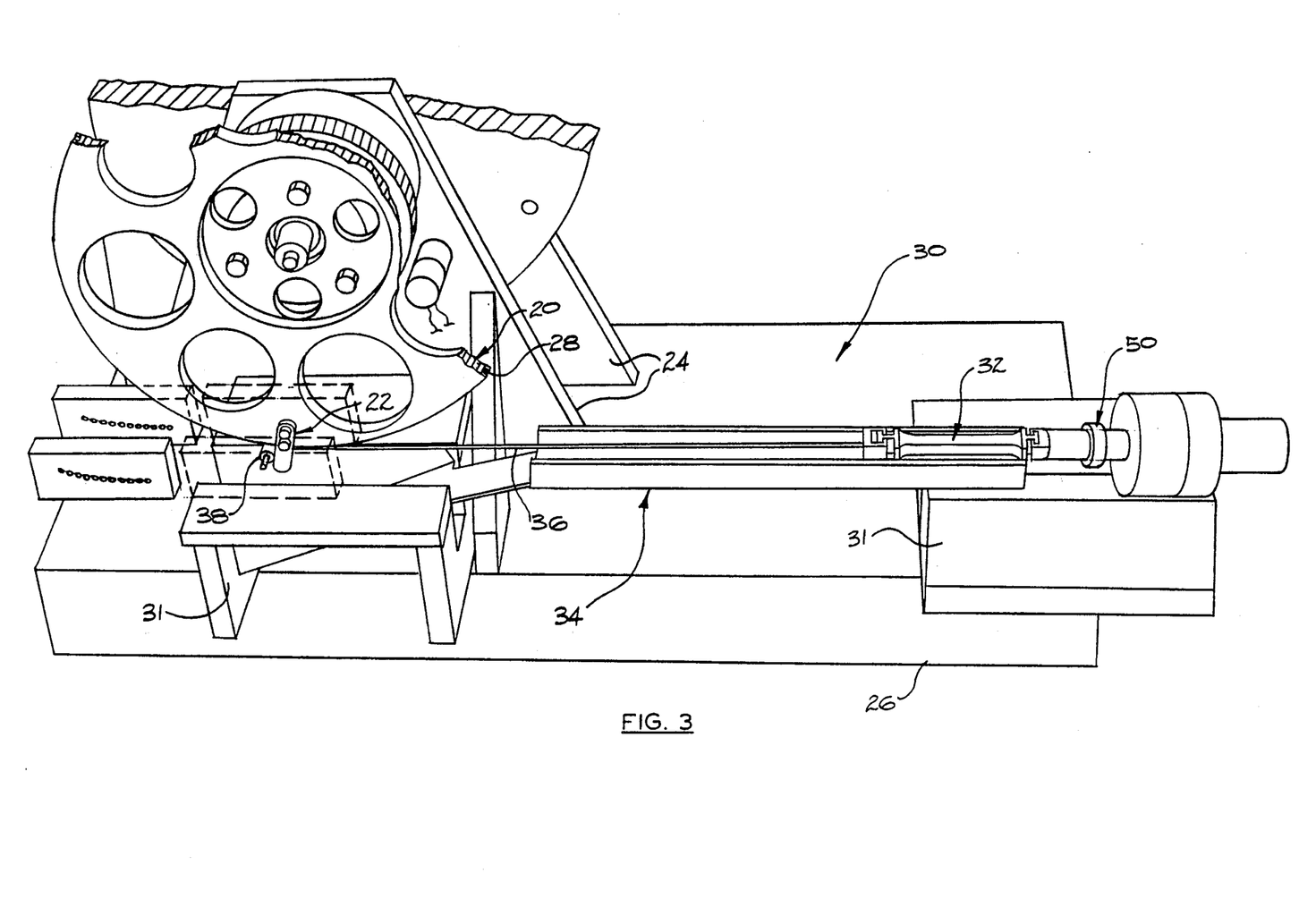
FIG. 3 is a detailed view of the stretching mechanism, and load cell used in the present invention. The support blocks have been moved to further illustrate the roll pin and engagement claw.

A stretching mechanism (30), as seen in FIG. 1 and FIG. 3, for elongating the viscoelastic test specimen (32) is located on a test stand (31) proximate the light weight engagement wheel (20) and further positioned so as to properly align the viscoelastic test specimen (32) with the light weight engagement wheel (20) and engagement claw (22). The light weight engagement wheel (20) is initially in a stationary or stopped position. When activated, the light weight engagement wheel (20) quickly ramps up to the desired speed and the engagement claw (22) engages the stretching mechanism (30) which initiates the high rate tensile test on the viscoelastic test specimen (32). The light weight engagement wheel (20) must ramp up to the desired speed in less than one full rotation of the engagement wheel (20) after the clutch and rotor assembly (15) initiate the engagement wheel (20).

The stretching mechanism (30) is preferably comprised of an aluminum channel guide (34) which is mounted to the test stand (31) and dimensioned to accommodate the viscoelastic test specimen (32). The test stand (31) is further mounted on the common base (26). In the channel guide (34) is the test specimen (32) and a length of wire (36) having one end attached to the test specimen (32) and the other end crimped to a roll pin (38) which is located near the light weight engagement wheel (20) and positioned for engagement by the engagement claw (22). The roll pin (38) and length of wire (36) are further positioned so as to tangentially align the viscoelastic test specimen (32) with the light weight engagement wheel (20).

Figure 4:
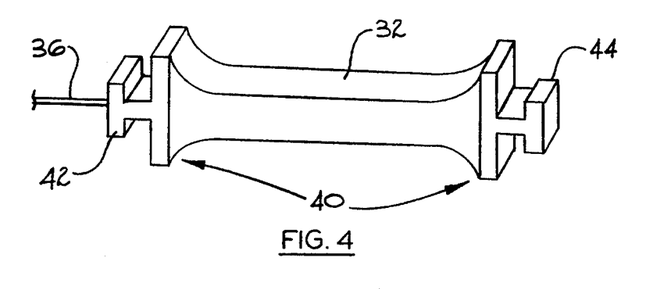
FIG. 4 is a detailed view of the viscoelastic test specimen secured in the test specimen brace as it appears when used with the present invention.

FIG. 4 depicts a detailed view of the viscoelastic test specimen (32) as it appears in the preferred embodiment of the present invention. The test specimen (32) is secured in a test specimen brace (40). The test specimen brace has a forward end (42) and an aft end (44). The aft end (44) of the test specimen brace (40) is attached to a tension-compression load cell (50) or load transducer. The forward end (42) of the test specimen brace (40) is secured to one end of a length of piano wire (36). The piano wire (36) is preferably 0.025 inch diameter wire which is adapted for placement within the outer diameter groove (28) in the light weight aluminum engagement wheel (20). As discussed above, the test specimen (32) and the length of piano wire (36) are disposed in an aluminum channel guide (34) which guides the test specimen (32) as it is elongated or stretched.

Figure 6:
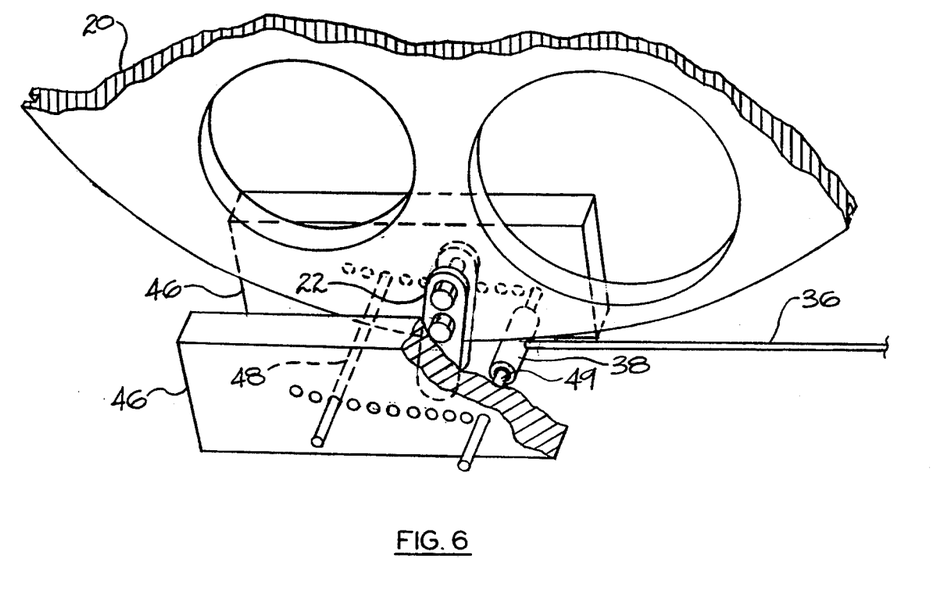
FIG. 6 is a partial perspective view of the present invention depicting the support blocks, roll pin, breakable connectors and engagement claw.

Referring now to FIGS. 1 and FIG. 6, the preferred embodiment preferably includes two support blocks (46) which are used to keep the engagement wheel (20) stationary while the flywheel (14) accelerates. Breakable connectors (48, 49) are disposed between the two support blocks (46) and are placed in front and behind the engagement claw (22) thereby preventing unintentional movement of the engagement wheel (20) and rotor assembly (18). One of the breakable connectors (49) is adapted to hold the roll pin (38) in alignment with the engagement claw (22) and engagement wheel (20). As the clutch (16) engages, the rotor assembly (18) and engagement wheel (20) are forcibly initiated. This forced movement of the engagement wheel (20) and corresponding movement of the engagement claw (22) breaks the first breakable connector (48) allowing the engagement wheel (20) to make almost a complete revolution whereby it gains constant speed. The engagement claw (22) then hits the roll pin (38) and breaks the second breakable connector (49) allowing free movement of the roll pin (38) and piano wire (36). The test specimen (32) is subsequently pulled to failure.

Also present on the preferred embodiment of the invention is an opto-electronic reflective read head assembly (52) proximate the rotor assembly (18). As seen in FIG. 1 and FIG. 2, the rotor assembly (18) has a plurality of tick marks (54) placed circumferentially on the radial surface (56). The preferred opto-electronic assembly (52) is a photo-diode device (53) that registers the tick marks (54) on the radial surface (56) of the rotor assembly (18) to determine the rotational speed of the engagement wheel (20). The resulting voltage signal from the photo-diode (53) is recorded on a 2-channel oscilloscope (not shown). The preferred flywheel testing apparatus (10) utilizes a rotor assembly (18) having 82 equally spaced tick marks. The distance between each tick mark (54) on the radial surface (56) of the rotor assembly (18) is equivalent to 0.432 inch elongation of the test specimen (32). The oscilloscope (not shown) is activated electronically when the electromagnetic fast acting clutch is engaged.

The voltage output of the opto-electronic assembly (52) is preferably recorded on one of the two oscilloscope channels as a sinusoidal trace from which the straining rate and elongation of the test specimen (32)

are calculated. The second channel monitors the electrical output of the load cell (50). The resulting processing and comparison of the two signals yields quantitative assessments of the stress-strain characteristics of the viscoelastic material as well as total energy at break.

Figure 5:
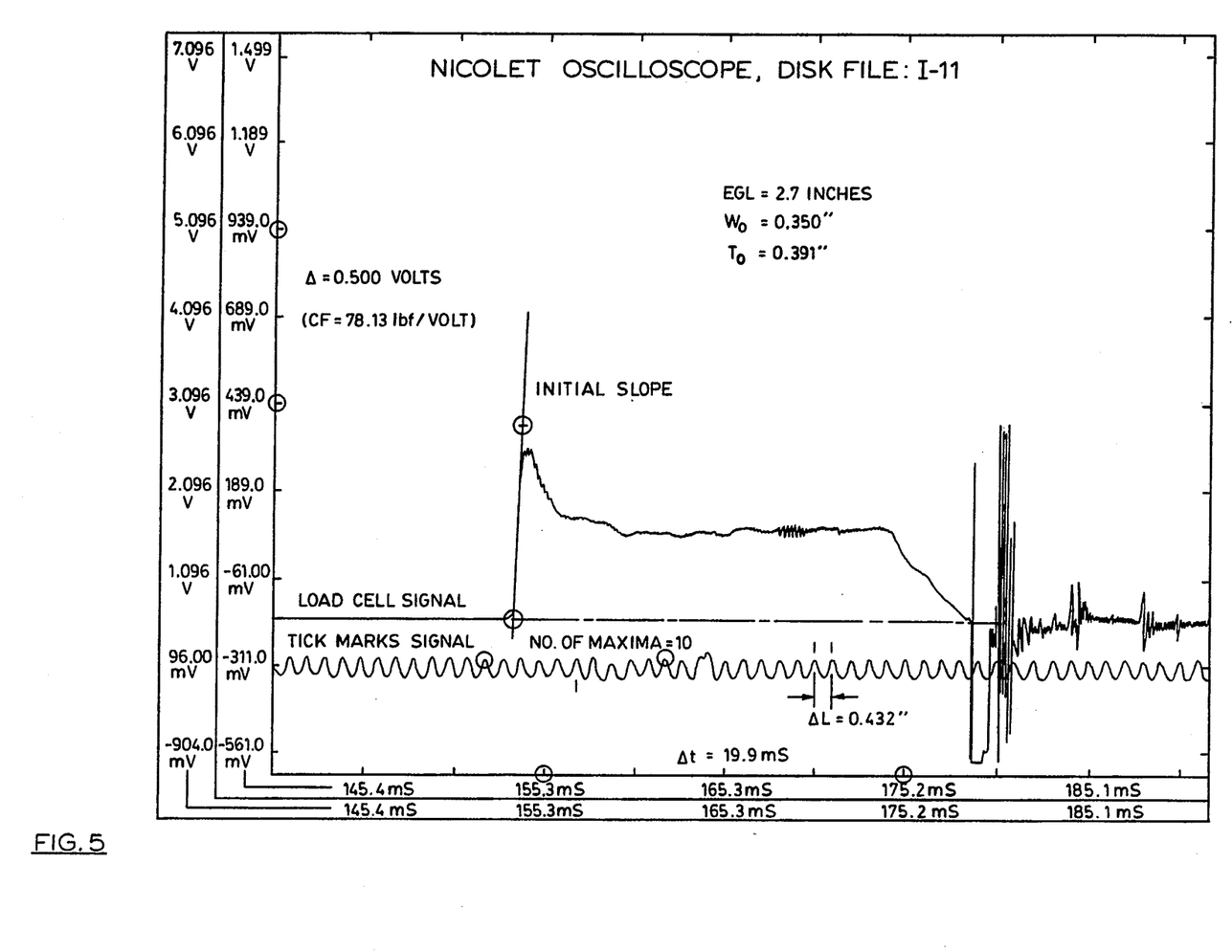
FIG. 5 is a stress-strain curve for a viscoelastic test specimen, the data being obtained from an actual tensile test utilizing the present invention.

FIG. 5 illustrates a stress-strain curve for an actual end-tabbed dogbone test specimen which was pulled to failure with the present invention as recorded on the two channel oscilloscope. The viscoelastic test specimen had an effective length of 2.7 inches and was subjected to an extension rate of approximately 26,400 inches per minute.

A major difficulty encountered in high-rate testing of viscoelastic materials is commonly known as the ringing of the load cell (50) or load transducer. Load cell ringing is always associated with such high-rate testing of materials and can introduce errors in the output of the load cell (50). Since the resonance frequency is a function of the spring constant and mass of the load cell (50). The impact of the engagement claw (22) with the roll pin (38) initiates a shock wave that travels through the wire (36) and test specimen (32) to the load cell (50) where it is reflected. The reflected shock wave acts as a forced vibration with a frequency which is dependent on the sound velocity in the viscoelastic materials. The sound wave velocity in a propellant is in the region of about 2,000 meters per second. The ratio between the forced frequency and the resonance frequency determines the elastic damping required for the tensile test apparatus (10) to reduce the load cell ringing to a minimum. Typically, a heavier load cell (50) with a high spring constant such as a 1000-lbs Photocon capacitance type load cell yields stress-strain curves with less superimposed vibration.

Another area of concern centers on the mechanical properties of the wire (36) or string that pulls the test specimen (32) to failure. The impact properties of this item affects the data collected relative to the initial slope and peak height of the stress-strain curve for the viscoelastic material. Both the empirically determined initial modulus and peak of the stress-strain curve decrease considerably if the wire (36) stretches during the elongation of the test specimen (32). To that end, different wire materials were employed including nylon cord, glass fibers, braided steel cable, soft iron wire, and various other composite materials. The use of a 0.025 inch diameter piano wire (36) is considered the best suitable material.

From the forgoing description, those skilled in the art will appreciate that all the objects, advantages and features of the present invention are realized. A high rate flywheel tensile test apparatus for determining mechanical properties of viscoelastic test specimens has been shown and described. While a specific embodiment has been shown and described, many different configurations are possible. The particular size of the flywheel (14), the engagement wheel (20), and the specifications of the motor may all be changed to suit the particular application to which it is used. The construction of the wire or string may vary, although piano wire is preferred. The instrumentation, measurement equipment, and associated electronic circuits for controlling the operation of the test apparatus may also be altered to suit the particular environment in which the test apparatus is employed.

Having described the invention in detail, those skilled in the art will appreciate that modification may be made to the invention without departing from its spirit, therefor it is not intended that the scope of the invention be limited to the specific embodiment illustrated and described. Rather, it is intended that the scope of this invention be determined by the appending claims and their equivalents.

What is claimed as the invention is:

1. A high rate tensile testing apparatus for Viscoelastic test specimens comprising:
   a plurality of support trestles mounted on a base;
   a flywheel mounted for rotation on the support trestles;
   a light weight engagement wheel mounted for rotation on the support trestles, the light weight engagement wheel further defining an engagement claw disposed on the periphery of the light weight engagement wheel;
   a rotor assembly disposed between the flywheel and the light weight engagement wheel and in operative association with the flywheel, the rotor assembly further adapted to engage the light weight engagement wheel;
   a clutch connected to the flywheel and adapted to engage the rotor assembly in response to a signal; and
   a stretching mechanism adapted for elongating the viscoelastic test specimen, the stretching mechanism disposed on the base and proximate to the light weight engagement wheel and further positioned so as to tangentially align the viscoelastic test specimen with the light weight engagement wheel and engagement claw.

2. A high rate tensile testing apparatus for viscoelastic test specimens comprising:
   a plurality of support trestles mounted on a base;
   a flywheel mounted for rotation on the support trestles;
   a light weight engagement wheel mounted for rotation on the support trestles, the light weight engagement wheel further defining an engagement claw disposed on the periphery of the light weight engagement wheel and further defining an outer diameter groove located on a peripheral surface of the light weight engagement wheel;
   a clutch and rotor assembly disposed between the flywheel and the light weight engagement wheel and in operative association with the flywheel, the clutch and rotor assembly further adapted to engage the light weight engagement wheel in response to a signal; and
   a stretching mechanism for adapted elongating the viscoelastic test specimen, the stretching mechanism disposed on the base and proximate to the .light weight engagement wheel and further positioned so as to tangentially align the viscoelastic test specimen with the light weight engagement wheel and engagement claw.

3. The high rate tensile testing apparatus of claim 2 wherein the stretching mechanism further comprises:
   a roll pin disposed on the base and proximate to the light weight engagement wheel and positioned for engagement by the engagement claw, the roll pin is further positioned so as to properly align the viscoelastic test specimen with the light weight engagement wheel; and
   a length of wire having one end attached to the viscoelastic test specimen and the other end crimped to the roll pin which is subsequently engaged by the engagement claw thereby elongating the viscoelastic test specimen, the length of wire is further adapted for fitting in the outer diameter groove of the light weight engagement wheel as the light weight engagement wheel rotates and the viscoelastic test specimen stretches.

4. The high rate tensile testing apparatus of claim 2 wherein the stretching mechanism further comprises:

a channel guide mounted to the base and adapted for receiving the viscoelastic test specimen;

a roll pin disposed on the base and proximate to the light weight engagement wheel and positioned for engagement by the engagement claw, the roll pin is further positioned so as to properly align the viscoelastic test specimen with the light weight engagement wheel;

a test specimen brace having a forward end and an aft end both of which are bonded to the viscoelastic test specimen, the test specimen brace disposed in the channel guide and further aligned with the roll pin so that the viscoelastic test specimen can be elongated when the engagement wheel is initiated; and a length of wire having one end attached to the forward end of the test specimen brace and the other end crimped to the roll pin which is subsequently engaged by the engagement claw thereby elongating the viscoelastic test specimen, the length of wire is further adapted for fitting in the outer diameter groove of the light weight engagement wheel as the light weight engagement wheel rotates and the viscoelastic test specimen stretches.

5. The high rate tensile testing apparatus of claim 4 wherein the length of wire is a length of piano wire.

6. The high rate tensile testing apparatus of claim 2 wherein the clutch and rotor assembly further comprises:

a rotor assembly disposed between the flywheel and the light weight engagement wheel and in operative association with the flywheel, the rotor assembly further adapted for rotating the light weight engagement wheel; and a clutch connected to the flywheel and adapted to engage the rotor assembly in response to a signal.

7. The high rate tensile testing apparatus of claim 6 wherein the clutch is an electromagnetic fast acting clutch.

8. The high rate tensile testing apparatus of claim 2 further comprising a variable speed motor mounted to the base and adapted for imparting rotational energy to the flywheel.

9. The high rate tensile testing apparatus of claim 2 further comprising a measurement means for collecting empirical data relating to the mechanical properties of the viscoelastic test specimen during the high rate tensile testing of the viscoelastic test specimen, the measurement means disposed on the base and proximate the stretching mechanism.

10. The high rate tensile testing apparatus of claim 9 wherein the measurement means further comprises a tension-compression load transducer attached to the viscoelastic test specimen for measuring the loads on the viscoelastic test specimen.

11. The high rate tensile testing apparatus of claim 10 wherein the measurement means further comprises:

a plurality of equally spaced tick marks disposed circumferentially around the rotor assembly on a radial surface of the rotor assembly; and a photo-diode device disposed proximate the rotor assembly, the photo-diode device adapted for generating a signal corresponding to the tick marks on the radial surface of the rotor assembly which pass the photo-diode device in order to determine the rotational speed of the rotor assembly and the engagement wheel.

12. A high rate tensile testing apparatus for viscoelastic test specimens comprising:

a base;

a plurality of support trestles mounted on the base;

a flywheel mounted for rotation on the support trestles;

a variable speed motor mounted to the base and adapted for imparting rotational energy to the flywheel;

a light weight engagement wheel mounted for rotation on the support trestles, the light weight engagement wheel further defining an outer diameter groove located on a peripheral surface of the light weight engagement wheel;

a rotor assembly disposed between the flywheel and the light weight engagement wheel and in operative association with the flywheel, the rotor assembly further adapted for rotating the light weight engagement wheel;

a plurality of equally spaced tick marks disposed circumferentially around the rotor assembly on a radial surface of the rotor assembly;

an electromagnetic fast acting clutch connected to the flywheel, said electromagnetic fast acting clutch adapted to engage the rotor assembly in response to a signal;

an engagement claw mounted on the periphery of the light weight engagement wheel;

a channel guide mounted to the base and adapted for receiving the viscoelastic test specimen;

a roll pin disposed on the base and proximate to the light weight engagement wheel and positioned for engagement by the engagement claw, the roll pin is further positioned so as to properly align the viscoelastic test specimen with the light weight engagement wheel;

a test specimen brace having a forward end and an aft end both of which are bonded to the viscoelastic test specimen, the test specimen brace disposed in the channel guide and further aligned with the roll pin so that the viscoelastic test specimen can be elongated when the engagement wheel is initiated;

a length of wire having one end attached to the forward end of the test specimen brace and the other end crimped to the roll pin which is subsequently engaged by the engagement claw thereby elongating the viscoelastic test specimen, the length of wire is further adapted for fitting in the outer diameter groove of the light weight engagement wheel as the light weight engagement wheel rotates and the viscoelastic test specimen stretches;

a tension-compression load transducer attached to the aft end of the test specimen brace for measuring the loads on the viscoelastic test specimen; and a photo-diode device disposed proximate the rotor assembly, the photo-diode device adapted for generating a signal corresponding to the tick marks on the radial surface of the rotor assembly which pass the photo-diode device in order to determine the rotational speed of the rotor assembly and the engagement wheel.

13. A method for high rate tensile testing of viscoelastic test specimens comprising the steps of:

mounting a plurality of support trestles to a base;

mounting for rotation a flywheel on the support trestles;

mounting for rotation a light weight engagement wheel on the support trestles, the light weight engagement wheel further defining an engagement claw disposed on the periphery of the light weight engagement wheel;

operatively connecting the light weight engagement wheel and the flywheel with a clutch and rotor assembly disposed between the flywheel and the light weight engagement wheel, the clutch and rotor assembly further adapted to engage the light weight engagement wheel in response to a signal;

placing a stretching mechanism on the base and proximate the engagement wheel so as to tangentially align the viscoelastic test specimen with the light weight engagement wheel and engagement claw, the stretching mechanism adapted for elongating the viscoelastic test specimen;

rotating the flywheel to a predetermined velocity with a variable speed motor adapted for imparting rotational energy to the flywheel;

activating the clutch and rotor assembly thereby engaging for rotation the light weight engagement wheel causing the engagement claw to strike the stretching mechanism and pull the viscoelastic test specimen to failure;

collecting empirical data relating to the mechanical properties of the viscoelastic test specimen during the high rate tensile testing of the viscoelastic test specimen utilizing various measurement equipment disposed on the base and proximate the stretching mechanism.

14. The method for high rate tensile testing of viscoelastic test specimens of claim 13 wherein the step of placing a stretching mechanism proximate the engagement wheel further comprises the following steps:

placing a channel guide on the base and adapted for receiving the viscoelastic test specimen;

placing a roll pin proximate to the light weight engagement wheel and positioned for engagement by the engagement claw, the roll pin is further positioned so as to tangentially align the viscoelastic test specimen with the light weight engagement wheel;

placing the viscoelastic test specimen in a test specimen brace, the test specimen brace having a forward end and an aft end both of which are bonded to the viscoelastic test specimen, the test specimen brace disposed in the channel guide and further aligned with the roll pin so that the viscoelastic test specimen can be elongated when the engagement wheel is initiated;

connecting one end of a length of wire to the forward end of the test specimen brace; and crimping the other end of the length of wire to the roll pin which is subsequently engaged by the engagement claw thereby pulling the length of wire and elongating the viscoelastic test specimen.

15. The method for high rate tensile testing of viscoelastic test specimens of claim 14 wherein the step of placing a clutch and rotor assembly proximate the engagement wheel further comprises the following steps:

connecting a rotor assembly between the flywheel and the light weight engagement wheel, the rotor assembly further adapted for rotating the light weight engagement wheel; and connecting a fast acting electromagnetic clutch to the flywheel, the electromagnetic fast acting clutch is further adapted to engage the rotor assembly in response to an external signal thereby transferring the stored energy from the flywheel to the light weight engagement wheel.

16. The method for high rate tensile testing of viscoelastic test specimens of claim wherein the length of wire is 0.025 inch diameter piano wire.

17. The method for high rate tensile testing of viscoelastic test specimens of claim 16 wherein the step of collecting data utilizing measurement equipment further comprises the steps of:

attaching a tension-compression load transducer to the viscoelastic test specimen for measuring the loads on the viscoelastic test specimen; and attaching a photo-diode device proximate the rotor assembly, the photo-diode device adapted for generating a signal corresponding to tick marks which are placed on the radial surface of the rotor assembly when the tick marks pass the photo-diode device.

* * * * *